Figure 1:
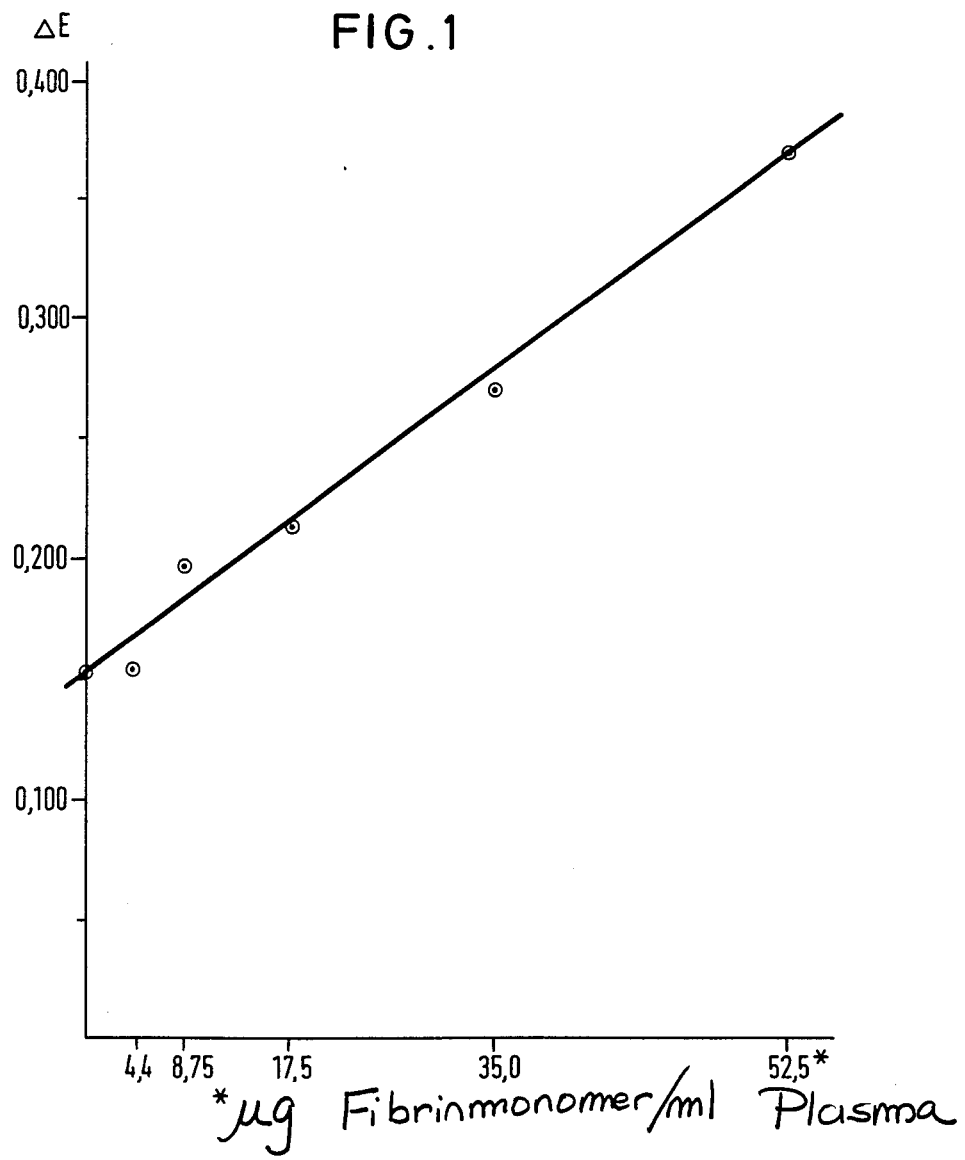

United States Patent [19]

Bartl et al.

[11] Patent Number: 4,710,459

[45] Date of Patent: Dec. 1, 1987

[54] PROCESS AND REAGENT FOR THE DETERMINATION OF FIBRIN MONOMER IN PLASMA

[75] Inventors: Knut Bartl, Wilzhofen; Helmut Lill, Wielenbach, both of Fed. Rep. of Germany

[73] Assignee: Boehringer Mannheim GmbH, Mannheim, Fed. Rep. of Germany

[21] Appl. No.: 767,865

[22] Filed: Aug. 21, 1985

[30] Foreign Application Priority Data

Aug. 22, 1984 [DE] Fed. Rep. of Germany ....... 3430906

[51] Int. Cl.$^4$ .................... C12Q 1/56; C12N 9/74; C12N 9/68
[52] U.S. Cl. ..................... 435/13; 435/214; 435/217; 435/810; 436/63; 436/69
[58] Field of Search .................... 435/13, 214, 217; 436/63, 69

[56] References Cited

U.S. PATENT DOCUMENTS 4,429,040 1/1984 Becker et al. .................. 435/13
4,563,420 1/1986 Verheijen et al. ................ 435/13

FOREIGN PATENT DOCUMENTS 011463 5/1980 European Pat. Off. .
094720 11/1983 European Pat. Off. .
8100578 3/1981 World Int. Prop. O. .

OTHER PUBLICATIONS

Ranby et al., *Thrombosis Research*, 27; 743–749, 1982.
Raanby et al, *Prog. Fibrinolysis* (1981), 5, 233–5 (abstract only, CA: vol. 98 (1983): 49234s).

*Primary Examiner*—Christine M. Nucker
*Attorney, Agent, or Firm*—Felfe & Lynch

[57] ABSTRACT

The present invention provides a process for the determination of fibrin monomer in plasma, wherein a plasma sample containing fibrin monomer and freed from plasmin inhibitors is incubated in buffered solution with tissue plasminogen activator (EPA), plasminogen and a chromogenic plasmin substrate and the color formed is measured as a measure of the amount of fibrin monomer.

The present invention also provides a reagent for the determination of fibrin monomer in plasma, wherein it contains plasminogen, tissue plasminogen activator (EPA), chromogenic plasmin substrate and buffer (pH 7.0 to 9.0).

5 Claims, 2 Drawing Figures

PROCESS AND REAGENT FOR THE DETERMINATION OF FIBRIN MONOMER IN PLASMA

The present invention is concerned with a process for the determination of fibrin monomer in plasma and a reagent suitable for this purpose.

The recognition of a readiness to thrombosis plays an important part in clinical diagnosis, for example before or after operations. One test parameter for the recoagnition of such a readiness to thombosis is the amount of fibrin monomer present in the serum. A content of fibrin monomer which increases above the normal value indicates a latent occurring cogulation process. For the determination of fibrin monomer in plasma, there are already known various methods, all of which, however, suffer from disadvantages. Thus, it is known to determine fibrin monomer by precipitation with ethanol or protamine sulphate. These precipitation methods contain the danger of a non-specific precipitation. Since they are also not sufficiently sensitive, they only give qualitative indications.

Determination methods by gel chromatography or affinity chromatography on fibrin-agarose are also known. These processes are not only not sufficiently sensitive but are also too laborious in order to be practicable for routine diagnosis.

An agglutination process with erythrocytes is also known in which erthrocytes have been previously loaded with fibrin monomer. This process also displays an unsatisfactory sensitivity.

Furthermore, a radioactive process is known in which $^{14}$C-glycine from appropriately marked glycine esters is incorporated into fibrin with the help of factor XIII. This process is admittedly sufficiently sensitive but requires the laborious measures and devices usual in the case of handling radioactive substances.

Finally, published European Patent Specification No. 0139885 discloses a turbidimetric process for the determination of fibrin monomer in plasma in which hydrophobic latex particles are mixed in a cuvette with sample and buffer and the extinction increase is measured as a result of the aggregation of the latex particles. The process is admittedly very sensitive with a limit of detection of about 1.2 $\mu$g./ml. and is suitable for routine diagnosis. However, it depends upon a non-specific adsorption and can, therefore, be subject to disturbances.

It is an object of the present invention to provide a process of the above-mentioned kind which does not possess the mentioned disadvantages of the known processes, is based upon a specific biochemical basis, is very sensitive and can be carried out by simple colour measurement in the visible range.

Thus, according to the present invention, there is provided a process for the determination of fibrin monomer in plasma, wherein a plasma sample containing fibrin monomer and freed from plasmin inhibitors is incubated in buffered solution with tissue plasminogen activator (EPA), plasminogen and a chromogenic plasmin substrate and the colour formed is measured as a measure of the amount of fibrin monomer.

The process according to the present invention is based upon the fact that, under the influence of thrombin, fibrin monomer is formed from fibrinogen with the splitting off of fibrinopeptide A. Fibrin monomer formed in turn activates EPA, EPA leads to plasmin formation from plasminogen and the plasmin formed, which itself initiates the fibrinolysis reaction, splits the chromogenic substrate provided. Thus, the process according to the present invention utilises the activating effectiveness of fibrin monomer with regard to EPA.

For the process according to the present invention, the plasma sample to be investigated must first be freed from plasmin inhibitors, various methods being available for this purpose. According to a first preferred embodiment, the plasma to be investigated is mixed with acid with the formation of a precipitate which is separated off, for example by centrifuging, and is then suspended in buffer solution and used in the process as "plasma sample". As acid, there can be used any desired organic or inorganic acid, acetic acid being preferred. The amount to be added is preferably from 0.1 to 0.5% by volume, preferably about 0.2% by volume, referred to the plasma volume. The precipitation preferably takes place in a solution diluted with water, preferably diluted 1:5 to 1:15 with water. After the addition of the acid, the sample is left to stand for some time in the cold and the precipitate formed subsequently centrifuged off.

An alternative preferred method for the removal of the plasmin inhibitors consists in the incubation of the plasma to be investigated with a polystyrene body, the fibrin monomer hereby binding to the polystyrene surface. After some time, for example after 0.25 to 24 hours, the liquid can be poured off, the polystyrene body is carefully washed with water and the polystyrene body covered with the fibrin monomer is quasi used as sample. The sensitivity of the test can be increased by longer residence times. As polystyrene formed bodies, there can be used, for example polystyrene test tubes, polystyrene spheres, flocks and the like. In the case of using polystyrene test tubes, for example in the form of depressions in microtitre plates, the process according to the present invention can simply be carried out in such a manner that the test tubes are also used as measurement cuvettes, the other substances necessary for the determination being introduced in buffer solution into the test tubes and the colour formed is measured.

According to a further possibility for removing the plasmin inhibitors, the plasma to be investigated is mixed with polystyrene latex and moved about or left to stand for some time, the fibrin monomer thereby again forming on the surface of the polystyrene phase. The latex is then separated off and again used as sample in the above-described manner.

For the actual colour formation reaction, the test mixture is incubated for a time sufficient for the formation of the colour, for example for 0.5 to 5 hours, and the colour formed is then measured.

For carrying out the process according to the present invention, there is required not only tissue plasminogen activator (EPA), which is also called vascular plasminogen activator or extrinsic plasminogen activator, but also plasminogen, both substances being commercially available. Furthermore, there is used a chromogenic plasmin substrate, for example a plasmin substrate which contains p-nitroaniline. In the case of the incubation, the p-nitroaniline is liberated and can easily be measured at 405 nm. Such plasmin substrates are known and some of them are commercially available, for example Tos-Gly-Pro-Lys-p-nitroanilide and D-Val-Leu-Lys-p-nitroanilide. Other suitable chromogenic plasmin substrates include the aminoanilides corresponding to the mentioned nitroanilides, in combination with a coupling component and an oxidation agent.

The present invention also provides a reagent for the determination of fibrin monomer in plasma, which contains plasminogen, EPA, a chromogenic plasmin substrate and buffer (pH 7.0 to 9.0).

The reagent according to the present invention preferably contains 0.1 to 2.0 U/ml. plasminogen, 0.1 to 10 units of tissue plasminogen activator (EPA), 0.02 to 2.0 mMole/liter of chromogenic plasmin substrate and 0.01 to 2.0 mole/liter of buffer.

In addition, the reagent according to the present invention can also contain a surface-active agent, preferably a non-ionic surface-active agent, such as Tween 80. In this case, the concentration thereof is preferably from 0.01 to 1.0% by volume.

As buffer substance, there can be used any substance which buffers in the given range of from 7.0 to 9.0, the preferred buffer being tris buffer.

One unit of plasminogen is referred to Tos-Gly-Pro-Lys-p-nitroaniline as substrate, 37° C. and measurement of the plasminogen-streptokinase complex. The above-mentioned unit of EPA is defined as the amount which, under the given test conditions but tested with saturated amounts of fibrin monomer gives, within an incubation period of 2 hours at 25° C., an extinction increase at 405 nm of 1.0.

Thus, the present invention provides the possibility of determining a readiness to thrombosis which is specific and highly sensitive by means of a simple process.

The following Examples are given for the purpose of illustrating the present invention:

EXAMPLE 1

Reagent:
plasminogen 0.8 U/ml. plasmin substrate Tos-Gly-Pro-Lys-p-nitroaniline 0.3 mMole/liter EPA 2 μg. (about 1.0 Unit) tris-HCl, 0.07 mole/liter, pH 7.5 Tween 80, 0.07% by volume.

Carrying out of the test:
Plasma was mixed with increasing amounts of fibrin monomer. Each 100 μl. of plasma were mixed with 900 μl. of ice-cold water and 75 μl. of 0.25% acetic acid. The mixture was then left to stand for 30 minutes in ice and subsequently centrifuged for 10 minutes at 3000 r.p.m. The precipitate was dissolved in 700 μl. of buffer. Each 100 μl. of sample solution were mixed with 900 μl. of reagent solution. The mixture was then incubated for 2 hours at 25° C. and the extinction measured at 405 nm. The results obtained are shown in FIG. 1 of the accompanying drawings. In this Figure, the extinction is plotted against the added amount of fibrin monomer. This amount is thereby from 0 to 52.5 μg. of fibrin monomer per ml. of plasma.

EXAMPLE 2

Figure 2:
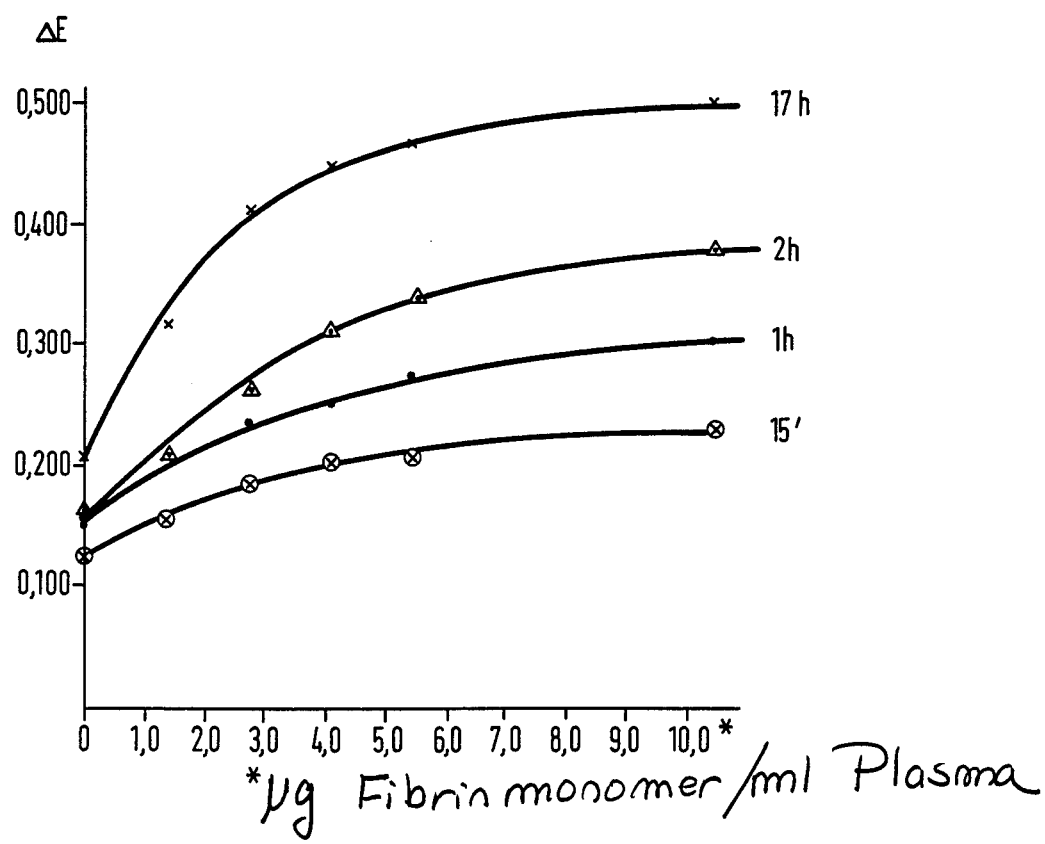

Plasma was mixed stepwise with fibrin monomer and then diluted with water in a ratio of 1:4. Each 250 μl. of plasma dilution were placed into the bores of a polystyrene microtitre plate. The plate was then left to stand at 4° C. and the sample subsequently shaken out and rinsed with water. Thereafter, 250 μl. amounts of reagent, as in Example 1, were introduced, incubated for 2 hours at 25° C. and the extinction subsequently measured at 405 nm. The results obtained are shown in FIG. 2 of the accompanying drawings. The curves give the results in the case of different residence periods of the plasma in the mcrotitre plate, the periods of residence thereby being from 15 minutes to 17 hours.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Process for the determination of fibrin monomer in plasma, comprising incubating a plasma sample containing fibrin monomer and freed from plasmin inhibitors in buffered solution with tissue plasminogen activator (EPA), plasminogen and a chromogenic plasmin substrate to form a color and measuring color formed to determine the amount of fibrin monomer present in said sample.

2. Process according to claim 1, wherein the plasma sample is obtained by mixing plasma with acid to form a precipitate, separating the precipitate formed and resuspending the precipitate in buffer solution.

3. Process according to claim 2, wherein said acid is acetic acid.

4. Process according to claim 1, wherein the plasma sample is obtained by incubating the plasma containing a fibrin monomer with a polystyrene body, to bind fibrin monomer to said body, and removing liquid from the sample.

5. Process according to claim 1, wherein the plasma sample is obtained by mixing the plasma containing a fibrin monomer with polystyrene latex and incubating to bind fibrin monomer to said polystyrene latex.

* * * * *